United States Patent [19]

O'Sullivan et al.

[11] Patent Number: 4,859,657
[45] Date of Patent: Aug. 22, 1989

[54] PESTICIDES

[75] Inventors: Anthony C. O'Sullivan, Basel; Bruno Frei, Liestal, both of Switzerland

[73] Assignee: Ciba-Geigy Corporation, Ardsley, N.Y.

[21] Appl. No.: 68,692

[22] Filed: Jun. 30, 1987

[30] Foreign Application Priority Data

Jul. 2, 1986 [CH] Switzerland .......................... 2668/86

[51] Int. Cl.$^4$ .................... A61K 31/35; C07D 313/08; C07D 309/10
[52] U.S. Cl. ..................................... 514/63; 514/450; 549/214; 549/264
[58] Field of Search ................ 549/264, 214; 514/450, 514/63

[56] References Cited

U.S. PATENT DOCUMENTS

| | | | |
|---|---|---|---|
| 4,093,629 | 6/1978 | Fisher | 260/326.34 |
| 4,134,973 | 1/1979 | Fisher et al. | 424/180 |
| 4,156,720 | 5/1979 | Fisher | 424/180 |
| 4,199,569 | 4/1980 | Chabala et al. | 424/180 |
| 4,200,581 | 4/1980 | Fisher et al. | 424/180 |
| 4,201,861 | 5/1980 | Mrozik et al. | 536/7.1 |
| 4,203,976 | 5/1980 | Fisher et al. | 424/180 |
| 4,457,920 | 7/1984 | Mrozik | 424/180 |
| 4,696,945 | 9/1987 | Frei et al. | 514/450 |
| 4,778,809 | 10/1988 | Maienfisch | 514/450 |

FOREIGN PATENT DOCUMENTS

| | | | |
|---|---|---|---|
| 0184173 | 6/1986 | European Pat. Off. | |
| 2167751 | 6/1986 | United Kingdom | 536/7.1 |
| 2168345 | 6/1986 | United Kingdom | |

Primary Examiner—Richard L. Raymond
Assistant Examiner—Mark W. Russell
Attorney, Agent, or Firm—Edward McC. Roberts

[57] ABSTRACT

Novel compounds of the formula

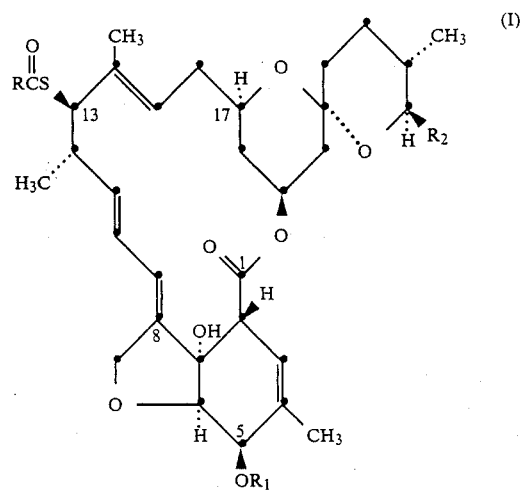

in which $R_1$ is a hydrogen or a silyl or acyl group, $R_2$ is methyl, ethyl, isopropyl or sec.-butyl and R is hydrogen, unsubstituted or substituted, linear or branched-chain $C_1$–$C_{18}$-alkyl groups, unsubstituted or substituted cycloaliphatic groups having 3 to 10 carbon atoms, unsubstituted or substituted $C_2$–$C_6$-alkenyl groups, unsubstituted or substituted $C_2$–$C_6$-alkynyl groups, unsubstituted or substituted phenyl groups or unsubstituted or substituted benzyl groups. The active compounds possess advantageous pesticidal properties. They are particularly suitable for the control of pests in agriculture and the management of stored products.

15 Claims, No Drawings

PESTICIDES

The present invention relates to novel 13 β-milbemycin derivatives of the formula I, to their preparation and to their use for controlling pests, and also to pest control compositions containing at least one of these compounds as the active substance.

The novel compounds have the general formula I

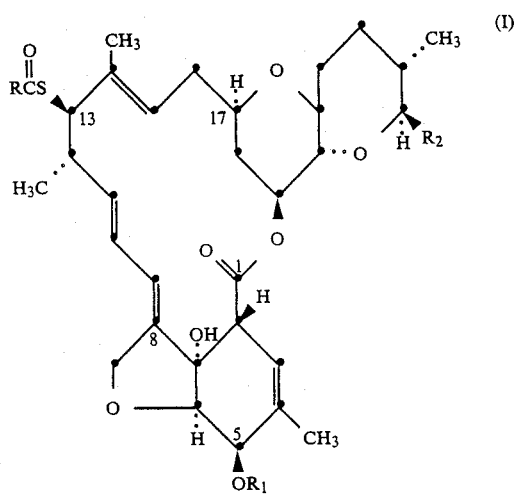

in which $R_1$ is a hydrogen or a silyl or acyl group, $R_2$ is methyl, ethyl, isopropyl or sec.-butyl and R is hydrogen, unsubstituted or substituted, linear or branched-chain $C_1$–$C_{18}$-alkyl groups, unsubstituted or substituted cycloaliphatic groups having 3 to 10 carbon atoms, unsubstituted or substituted $C_2$–$C_6$-alkenyl groups, unsubstituted or substitued $C_2$–$C_6$-alkynyl groups, unsubstituted or substituted phenyl groups or unsubstituted or substituted benzyl groups.

Amongst the abovementioned meanings of R, the following are to be regarded as preferred: unsubstituted or halogenated $C_1$–$C_8$-alkyl; $C_3$–$C_6$-cycloalkyl which is unsubstituted or monsubstituted or polysubstituted by methyl; and adamantyl; and unsubstituted or halogenated $C_2$–$C_6$-alkenyl and $C_2$–$C_6$-alkynyl.

Examples of suitable substituents in the alkyl, cycloalkyl, alkenyl and alkynyl groups are 1 to 7 halogen atoms or 1 to 6 $C_1$–$C_6$-alkoxy groups, and suitable substituents in the phenyl and benzyl groups are 1 to 3 substituents selected from the group consisting of halogen atoms, $C_1$–$C_6$-alkyl, $C_1$–$C_6$-alkoxy, $C_1$–$C_4$-alkylthio, phenyl or nitro. Benzyl groups can be substituted both on the ring and on the aliphatic carbon atom, for example α-methylbenzyl and α, α-dimethylbenzyl. R can also be an alkyl group carrying one of the substituents mentioned below: an unsubstituted or substituted phenoxy group, for example a halogenated phenoxy group, especially a phenoxy group substituted by 1 to 3 halogen atoms; a $C_1$–$C_4$-alkylthio group, a $C_1$–$C_4$-alkylcarbonyl group or $C_3$–$C_6$-cycloalkyl which can be monosubstituted or polysubstituted by methyl. In addition to the substituents alreayd mentioned earlier in the text, $C_1$–$C_4$-alkyl groups can also be present as substituents in the cycloalkyl groups which are immediately attached to the carbonylthio group. Aromatic rings can also contain halogeno-$C_1$–$C_4$-alkyl and amine as substituents, it being possible for the substituents to be identical or different or for only one of the substituents to be present, and the phenyl group can also be substituted by a difluoromethylenedioxy group, the two oxygen atoms being located on two adjacent ring carbon atoms.

Depending on the number of carbon atoms indicated, the term alkyl, as a substituent or part of a substituent, is to be understood as meaning the following groups, for example: methyl, ethyl, propyl, butyl, pentyl, hexyl, heptyl, octyl, nonyl or decyl, and the isomers, for example isopropyl, isobutyl, tert.-butyl or isopentyl. Halogenoalkyl is a monohalogenated to perhalogenated alkyl substituent, for example $CHCl_2$, $CHF_2$, $CH_2Cl$, $CCl_3$, $CF_3$, $CH_2F$, $CH_2CH_2Cl$ or $CHBr_2$. Here and in the following text, halogen is to be understood as meaning fluorine, chlorine, bromine or iodine, preferably fluorine, chlorine or bromine. Suitable cycloaliphatic groups are monocyclic to tetracyclic groups, for example cyclopropyl, cyclobutyl, cyclopentyl, cyclohexyl, decalin, hydrindane, bicycloheptane, bicyclooctane, norbornane, bornane or adamantyl. These cycloaliphatic groups are preferably unsubstituted or are monosubstituted or polysubstituted by methyl. Alkenyl is an aliphatic, acyclic hydrocarbon radical characterized by at least one C=C double bond, for example vinyl, propen-1-yl, allyl, buten-1-yl, buten-2-yl or buten-3-yl. Accordingly, halogenoalkenyl is an alkenyl radical of this type which is monohalogenated or polyhalogenated. Alkynyl is a linear or branched carbon chain characterized by at least one C≡C triple bond. Examples of typical representatives are ethynyl, propyn-1-yl, propargyl or butyn-1-yl. Alkoxyalkyl is an unbranched or branched alkyl group which is interrupted by a oxygen atom, for example $CH_2OCH_3$, $CH_2CH_2OCH_3$, $CH_2CH(CH_3)OCH_3$, $CH_2OC_2H_5$, $C(CH_3)_2OCH_3$, $CH_2OC_3H_7$-i or $CH_2CH_2CH_2OCH_3$. These ether groups can also be mentioned as representatives of alkylthioalkyl groups—if O is replaced by S.

Suitable examples of substituted phenyl are 2,4-dichlorophenyl, 2,3,6-trichlorophenyl, p-bromophenyl, 2,4-xylyl, 3-nitrophenyl, o-(trifluoromethyl)-phenyl, 4-chloro-2-methylphenyl, 4-methyl-2-methoxyphenyl, 2,4,6-trimethylphenyl, p-aminophenyl or p-methylthiophenyl.

The following, which do not represent a limitation, should be mentioned as examples of R: hydrogen, methyl, ethyl, propyl, isopropyl, n-butyl, sec.-butyl, tert.-butyl, neopentyl, chloromethyl, trifluoromethyl, trichloromethyl, trichloroethyl, trichloro-tert.-butyl, 1,2,2,2-tetrachloroethyl, 1,3,3,3-tetrachloropropyl, 3-chloropropyl, ethenyl, propenyl, propynyl, methoxymethyl, isopropoxymethyl, 1-methyl-1-methoxyethyl, 2,2-dimethylvinyl, 1,2,2-trichlorovinyl, 1,3,3,3-tetrachloropropyl, 1,1-dichloro-2,2,2-trifluoroethyl, 1,3-pentadienyl, ethynyl, 1-propynyl, 1-butynyl, cyclopropyl, 2,2-dimethylcyclopropyl 1-methylcyclopropyl, 2,2-dimethyl-3-(2,2-dichlorovinyl)-cyclopropyl, cyclobutyl, cyclopentyl, cyclohexyl, adamantyl, phenyl, benzyl, p-tolyl, p-chlorophenyl, 2,6-dichlorophenyl or 2,4-dinitrophenyl or 4-fluorophenoxymethyl.

Compounds of the formula I in which $R_1$ is hydrogen are preferred. As $R_1$, acyl and silyl groups are to be understood, in general, as protective groups. Examples of suitable acyl groups are the radicals $R_5$—C(O)— in which $R_5$ is $C_1$–$C_{10}$-alkyl, $C_1$–$C_{10}$-halogenoalkyl or a radical belonging to the group comprising phenyl and benzyl which is unsubstituted or substituted by substituents of the group consisting of halogen, $C_1$–$C_3$-alkyl, $C_1$—$C_3$-halogenoalkyl, $C_1$–$C_3$-alkoxy, $C_1$–$C_3$-halogenoalkoxy, cyano and nitro, and $R_5$ is preferably $C_1$–$C_6$-alkyl, $C_1$–$C_6$-halogenoalkyl or phenyl which is unsubstituted or substituted by halogen, $C_1$–$C_3$-alkyl, $CF_3$ or nitro. The acetyl group is particularly preferred. 5-O-Acetyl-13β-formylthiomilbemycin $A_4$ may be mentioned as an example of an acyl compound. A suitable silyl group for $R_1$ is the radical —$Si(R_6)(R_7)(R_8)$ in which $R_6$, $R_7$ and $R_8$, preferably independently of one another, are $C_1$–$C_4$-alkyl, benzyl or phenyl, and form, for example, one of the groups trimethylsilyl, diphenyl-tert.-butylsilyl, bis-(isopropyl)-methylsilyl or triphenylsilyl and, preferably, tert.-butyldimethylsilyl.

The present invention extends both to the individual diastereomers and to mixtures of diastereomers of compounds of the formula I.

Here and in the following text, compounds in which $R_2$ is sec.-butyl will also be included among the milbemycin derivatives, although they are derived from avermectin derivatives according to the customary system. Avermectin aglycones (having an OH group in the 13α-position) can, however, be converted into milbemycin homologues in accordance with U.S. Pat. No. 4,173,571.

In naturally occurring milbemycins ($R_1$=H; $R_2$=$CH_3$, $C_2H_5$ or iso-$C_3H_7$), the 13-position is occupied only by hydrogen atoms, instead of the ester group of the compounds, according to the invention, of the formula I, as is shown in the formula below:

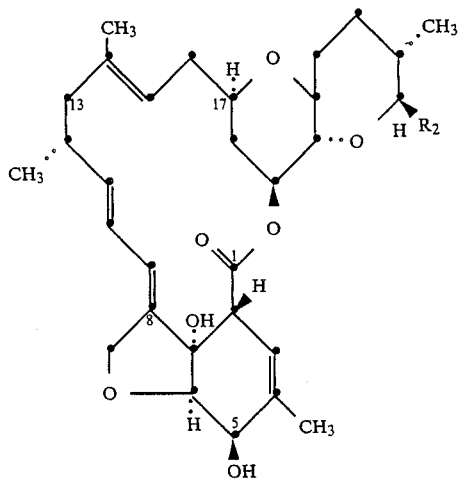

$R_2$=$CH_3$ milbemycin $A_3$ (U.S. Pat. No. 3,950,360)
$R_2$=$C_2H_5$ milbemycin $A_4$ (U.S. Pat. No. 3,950,360)
$R_2$=iso-$C_3H_7$ milbemycin D (U.S. Pat. No. 4,346,171)
$R_2$=sec.-$C_4H_9$ 13-deoxy-22,23-dihydro-C-076-B1a-aglycone. (U.S. Pat. No. 4,173,571, British Patent Specification 1,573,955 and German Offenlegungsschrift 2,717,040).

In avermectins, on the other hand, there is, in the 13-position, an α-L-oleandrosyl-α-L-oleandrose radical which is attached to the macrolide molecule via oxygen in the α-configuration. Additionally, avermectins differ structurally from the milbemycins in a 23-OH group or $\Delta^{22,23}$ double bond and, normally have a substituent $R_2$=sec.-$C_4H_9$. The corresponding avermectin aglycones which have a 13α-hydroxyl group located in an adjacent position to a C=C double bond are obtained readily by hydrolysing the sugar residue of the avermectins. As indicated above, the avermectin aglycones can be converted into the milbemycin homologues. In the milbemycin derivatives of the present application, the 22, 23 bond is saturated and the substituents in the 13-position is always in the β-configuration.

The following subgroups of compounds of the formula I are particularly preferred because of their pronounced parasiticidal and insecticidal action:

Group Ia: Compounds of the formula I in which $R_1$ is hydrogen, $R_2$ is methyl, ethyl, isopropyl or sec.-butyl and R is as defined below:
hydrogen or $C_1$–$C_6$-alkyl, $C_2$–$C_4$-alkenyl, $C_2$–$C_4$alkynyl or $C_3$–$C_6$-cycloalkyl, each of which unsubstituted or substituted by 1 to 4 halogen atoms or an $C_1$–$C_4$-alkoxy group;
phenyl which is unsubstituted or monosubstituted to trisubstituted by halogen, $C_1$–$C_4$-alkyl, $C_1$–$C_4$-alkoxy, $C_1$–$C_4$-alkylthio or nitro;

Group Ib: Compounds of the formula I in which $R_1$ is hydrogen, $R_2$ is methyl, ethyl, isopropyl or sec.-butyl and R is as defined below:
hydrogen or $C_1$–$C_4$-alkyl, $C_2$–$C_3$-alkenyl, $C_2$–$C_3$alkynyl or $C_3$–$C_6$-cycloalkyl, each of which is unsubstituted or substituted by 1 to 4 chlorine or fluorine atoms or a methoxy group; or
phenyl which is unsubstituted or substituted by chlorine, fluorine, $C_1$–$C_2$-alkyl, $C_1$–$C_2$-alkoxy, $C_1$–$C_2$-alkylthio or nitro;

Group Ic: Compounds of the formula I in which $R_1$ is hydrogen, $R_2$ is methyl or ethyl and R is as defined below:
hydrogen or $C_1$–$C_4$-alkyl, $C_2$–$C_3$-alkenyl, $C_2$–$C_3$-alkynyl or $C_3$–$C_6$-cycloalkyl, each of which unsubstituted or substituted by 1 to 4 chlorine of fluorine atoms or a methoxy group; or
phenyl which is unsubstituted or substituted by chlorine, fluorine, $C_1$–$C_2$-alkyl, $C_1$–$C_2$-alkyl, $C_1$–$C_2$-alkylthio or nitro;

Group Id: Compounds of the formula I in which $R_1$ is hydrogen, $R_2$ is isopropyl or sec.-butyl and R is as defined below:
hydrogen or $C_1$–$C_4$-alkyl, $C_2$–$C_3$-alkenyl, $C_2$–$C_3$-alkynyl or $C_3$–$C_6$-cycloalkyl, each of which unsubstituted or substituted by 1 to 4 chlorine or fluorine atoms or a methoxy group; or
phenyl which is unsubstituted or substituted by chlorine, fluorine, $C_1$–$C_2$-alkyl, $C_1$–$C_2$-alkoxy, $C_1$–$C_2$-alkylthio or nitro;

Gropu Ie: Compounds of the formula I in which $R_1$ is hydrogen, $R_2$ is methyl, ethyl, isopropyl or sec.-butyl and R is as defined below:
hydrogen or $C_1$–$C_4$-alkyl, $C_2$–$C_3$-alkenyl, $C_2$—$C_3$-alkynyl or $C_3$–$C_6$-cycloalkyl, each of which unsubstituted or substituted by 1 to 3 chlorine or fluorine atoms or a methoxy group; or
phenyl which is unsubstituted or substitted by chlorine, fluorine $C_1$–$C_2$-alkyl, $C_1$–$C_2$-alkoxy, $C_1$–$C_2$-alkylthio or nitro;

Group If: Compounds of the formula I in which $R_1$ is hydrogen, $R_2$ is methyl or ethyl and R is as defined below: hydrogen or $C_1$–$C_4$-alkyl, $C_2$–$C_3$-alkenyl, $C_2$–$C_3$-alkynyl or $C_3$–$C_6$-cycloalkyl, each of which unsubstituted or substituted by 1 to 3 chlorine or fluorine atoms or a methoxy group;

Group Ig: Compounds of the formula I in which $R_1$ is hydrogen, $R_2$ is isopropyl or sec.-butyl and R is as defined below: hydrogen or $C_1$–$C_4$-alkyl, $C_2$–$C_3$-alkenyl, $C_2$–$C_3$-alkynyl or $C_3$–$C_6$-cycloalkyl, each of which unsubstituted or substituted by 1 to 3 chlorine or fluorine atoms or a methoxy group;

Group Ih: Compounds of the formula I in which $R_1$ is hydrogen, $R_2$ is ethyl or isopropyl and R is as defined below: hydrogen, $C_1$–$C_8$-alkyl which is unsubstituted or is monosubstituted by $C_1$–$C_4$-alkoxy or by monohalogenated to trihalogenated phenoxy, or is substituted by 1 to 5 halogen atoms; a monocyclic to tetracyclic, aliphatic group which is unsubstituted or monosubstituted or polysubstituted by substituents of the group consisting of $C_1$–$C_4$-alkyl and halogenated $C_2$–$C_4$-alkenyl and has a total of 3 to 10 carbon atoms in the ring or ring system; monohalogenated to trihalogenated $C_2$–$C_4$-alkenyl or $C_3$–$C_4$-alkynyl or phenyl which is monosubstituted to trisubstituted by substituents of the group consisting of halogen, $C_1$–$C_4$-alkyl and nitro.

Group Ii: Compounds of the formula I in which $R_1$ is hydrogen, $R_2$ is ethyl or isopropyl and R is as defined below: hydrogen, $C_1$–$C_8$-alkyl which is unsubstituted or monosubstituted to trisubstituted by substituents of the group consisting of chlorine and fluorine, fluorophenoxymethyl, $C_3$–$C_4$-cycloalkyl which is unsubstituted by a methyl group; adamantyl, trichlorovinyl or monochlorophenyl.

Group Ik: Compounds of the formula I in which $R_1$ is hydrogen, $R_2$ is methyl or ethyl and R is as defined below: $C_1$–$C_7$-alkyl, $C_1$–$C_4$-alkyl which is monosubstituted by chlorine, fluorine, methoxy, methylthio, dimethylcyclohexyl or acetyl; phenyl which is monosubstituted by trifluoromethyl or the group —O—CF$_2$—O— in which the two oxygen atoms are located on two adjacent ring carbon atoms; phenyl which is monosubstituted to trisubstituted by substituents of the group consisting of chlorine and methyl, or α-methylbenzyl or α,α-dimethylbenzyl, each of which unsubstituted or substituted by 1 to 3 substituents of the group consisting of amino, halogen, $C_1$–$C_6$-alkyl, $C_1$–$C_6$-alkoxy, $C_1$–$C_4$-alkylthio, phenyl and nitro.

Group Il: Compounds of the formula I in which $R_1$ is hydrogen, $R_2$ is methyl or ethyl, preferably ethyl, and R is as defined below: $C_1$–$C_7$-alkyl which is unsubstituted or monosubstituted by halogen or $C_1$–$C_4$-alkoxy, phenyl which is monosubstituted by trifluoromethyl or the group —O—CF$_2$—O— in which the two oxygen atoms are located on two adjacent ring carbon atoms; or α-methylbenzyl or α,α-dimethylbenzyl.

Group Im: Compounds of the formula I in which $R_1$ is hydrogen, $R_2$ is methyl or ethyl, preferably ethyl, and R is as defined below: $C_1$–$C_7$-alkyl, $C_1$–$C_4$-alkyl which is monosubstituted by chlorine, fluorine or methoxy, phenyl which monosubstituted by trifluoromethyl or the group 'O—CF$_2$—O— in which the two oxygen atoms are located on two adjacent ring carbon atoms; or α-methylbenzyl or α,α-dimethylbenzyl.

Group In: Compounds of the formula I in which $R_1$ and $R_2$ are as defined for formula I and R is an α-methylbenzyl group which is substituted in the para-position by isobutyl, 1-cyclohexen-1-yl, phenyl or benzoyl, or R is an α-methyl-3-fluoro-4-phenylbenzyl group.

The following are examples of particularly preferred 5-hydroxy derivatives of the formula I:
13β-Formylthiomilbemycin D
13β-Acetylthiomilbemycin D
13β-Pivaloylthiomilbemycin D
13β-Formylthiomilbemycin $A_3$
13β-Acetylthiomilbemycin $A_3$
13β-Pivaloylthiomilbemycin $A_3$
13β-Formylthiomilbemycin $A_4$
13β-Acetylthiomilbemycin $A_4$
13β-(2′-Methoxy-2′-methylpropionylthio)-milbemycin D
13β-(2′-Methoxy-2′-methylpropionylthio)-milbemycin $A_4$
13β-Trichloroacetylthiomilbemycin $A_4$
13β-(4′-Chlorobutanoylthio)-milbemycin $A_4$
13β-Trichloroacryloylthiomilbemycin $A_4$
13β-Cyclopropanecarbonylthiomilbemycin $A_4$
13β-Cyclobutanecarbonylthiomilbemycin $A_4$
13β-Heptanoylthiomilbemycin $A_4$
13β-(3′-Chloro-2′,2′-dimethylpropionylthio)-milbemycin $A_4$
13β-(3′-Chloro-2′,2′-dimethylpropionylthio)-milbemycin $A_3$
13β-(1′-Methylcyclopropanecarbonylthio)-milbemycin $A_4$
13β-(1′-Methylcyclopropanecarbonylthio)-milbemycin $A_3$
13β-(1-Adamantanecarbonylthio)-milbemycin $A_4$
13β-(p-Fluorophenoxyacetylthio)-milbemycin $A_4$
13β-(2′-Chloro-2′-methylpropionylthio)-milbemycin $A_4$
13β-(2′,2′-Dichloropropionylthio)-milbemycin $A_4$
13β-(2′,2′-Dimethylbutanoylthio)-milbemycin $A_4$
13β-(3′,3′-Dimethylbutanoylthio)-milbemycin $A_4$
13β-(2′,2′,3′,3′-Tetramethylbutanoylthio)-milbemycin $A_4$
13β-(p-Chlorobenzoylthio)-milbemycin $A_4$
13β-(3′,3′,3′-Trifluoropropionylthio)-milbemycin $A_4$
13β-Chloroacetylthiomilbemycin $A_4$
13β-(2′-Chloro-3′,3′,3′-trifluoropropionylthio)-milbemycin $A_4$
13β-(3′,3′,3′-Trifluoropropionylthio)-milbemycin $A_4$
13β-[o-(Trifluoromethyl)-benzoylthio]-milbemycin $A_4$
13β-(α,α-Dimethylbenzoylthio)-milbemycin $A_4$
13β-(2-n-Propyl-n-valeroylthio)-milbemycin $A_4$
13β-[(2,3-Difluoromethylenedioxy)-benzoylthio]-milbemycin $A_4$ *and especially*
13β-Pivaloylthiomilbemycin $A_4$
13β-(α-Methylbenzylcarbonylthio)-milbemycin $A_4$ and
13β-(Methoxyacetylthio)-milbemycin $A_4$.

The following are examples of preferred compounds of the formula I which are provided with a protective group on the 5-hydroxyl group:
5-O-tert.-Butyldimethylsilyl-13β-formylthiomilbemycin D
5-O-tert.-Butyldimethylsilyl-13β-acetylthiomilbemycin D
5-O-tert.-Butyldimethylsilyl-13β-pivaloylthiomilbemycin D
5-O-tert.-Butyldimethylsilyl-13β-formylthiomilbemycin $A_3$
5-O-tert.-Butyldimethylsilyl-13β-acetylthiomilbemycin $A_3$
5-O-tert.-Butyldimethylsilyl-13β-pivaloylthiomilbemycin $A_3$
5-O-tert.-Butyldimethylsilyl-13β-formylthiomilbemycin $A_4$
5-O-tert.-Butyldimethylsilyl-13β-acetylthiomilbemycin $A_4$
5-O-tert.-Butyldimethylsilyl-13β-pivaloylthiomilbemycin $A_4$ 5-O-tert.-Butyldimethylsilyl-13β-(2'-methoxy-2'-methylpropionylthio)-milbemycin D
5-O-tert.-Butyldimethylsilyl-13β-(2'-methoxy-2'-methylpropionylthio)-milbemycin $A_4$
5-O-tert.-Butyldimethylsilyl-13β-trichloroacetylthiomilbemycin $A_4$
5-O-tert.-Butyldimethylsilyl-13β-(4'-chlorobutanoylthio)milbemycin $A_4$
5-O-tert.-Butyldimethylsilyl-13β-trichloroacryloylthiomilbemycin $A_4$
5-O-tert.-Butyldimethylsilyl-13β-cyclopropanecarbonylthiomilbemycin $A_4$
5-O-tert.-Butyldimethylsilyl-13β-cyclobutanecarbonylthiomilbemycin $A_4$
5-O-tert.-Butyldimethylsilyl-13β-heptanoylthiomilbemycin $A_4$
5-O-tert.-Butyldimethylsilyl-13β-(3'-chloro-2',2'-dimethylpropionylthio)-milbemycin $A_4$
5-O-tert.-Butyldimethylsilyl-13β-(3'-chloro-2',2'-dimethylpropionylthio)-milbemycin $A_3$
5-O-tert.-Butyldimethylsilyl-13β-(1'-methylcyclopropanecarbonylthio)-milbemycin $A_4$
5-O-tert.-Butyldimethylsilyl-13β-(1'-methylcyclopropanecarbonylthio)-milbemycin $A_3$
5-O-tert.-Butyldimethylsilyl-13β-(1-adamantanecarbonylthio)milbemycin $A_4$
5-O-tert.-Butyldimethylsilyl-13β-(p-fluorophenoxyacetylthio)milbemycin $A_4$
5-O-tert.-Butyldimethylsilyl-13β-(2'-chloro-2'-methylpropionylthio)-milbemycin $A_4$
5-O-tert.-Butyldimethylsilyl-13β-(2',2'-dichloropropionylthio)-milbemycin $A_4$
5-O-tert.-Butyldimethylsilyl-13β-(2',2'-dimethylbutanoylthio)-milbemycin $A_4$
5-O-tert.-Butyldimethylsilyl-13β-(3',3'-dimethylbutanoylthio)-milbemycin $A_4$
5-O-tert.-Butyldimethylsilyl-13β-(2',2',3',3'-tetramethylbutanoylthio)-milbemycin $A_4$
5-O-tert.-Butyldimethylsilyl-13β-(p-chlorobenzoylthio)-milbemycin $A_4$
5-O-tert.-Butyldimethylsilyl-13β-(3',3',3'-trifluoropropionylthio)-milbemycin $A_4$
5-O-tert.-Butyldimethylsilyl-13β-chloroacetylthiomilbemycin $A_4$
5-O-tert.-Butyldimethylsilyl-13β-(2'-chloro-3',3',3'-trifluoropropionylthio)-milbemycin $A_4$
5-O-tert.-Butyldimethylsilyl-13β-(3',3',3'-trifluoropropionylthio)-milbemycin $A_4$
5-O-tert.-Butyldimethylsilyl-13β-(α-methylbenzylcarbonylthio)-milbemycin $A_4$
5-O-tert.-Butyldimethylsilyl-13β-(methoxyacetylthio)-milbemycin $A_4$
5-O-tert.-Butyldimethylsilyl-13β-[o-(trifluoromethyl)-benzoylthio]-milbemycin $A_4$
5-O-tert.-Butyldimethylsilyl-13β-(α,α-dimethylbenzoylthio)milbemycin $A_4$
5-O-tert.-Butyldimethylsilyl-13β-(2-n-propyl-n-valeroylthio)milbemycin $A_4$
5-O-tert -Butyldimethylsilyl-13β-[(2,3-difluoromethylenedioxy)-benzoylthio]-milbemycin $A_4$.

Compounds of the formula I which are of particular interest are those in which R is tert.-butyl and $R_1$ and $R_2$ are as defined for formula I, and, of these, in particular the compounds in which $R_1$ is hydrogen and $R_2$ is methyl, ethyl or isopropyl.

The present invention also relates to processes which make it possible to introduce a β-acylthio group selectively in the 13-position of milbemycin or 13-deoxy-22,23-dihydroavermectin aglycone derivatives and hence to obtain the highly active novel parasiticides and insecticides of the formula I, which can at the same time also be used for the formation of further derivatives.

The starting material for the preparation of thiol esters of the formula I in which RCOS— is in the β-position is a compound of the formula II

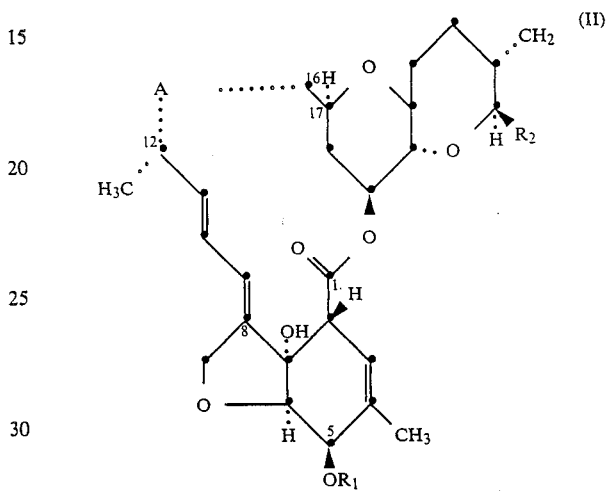

in which A is one of the groups a, b or c

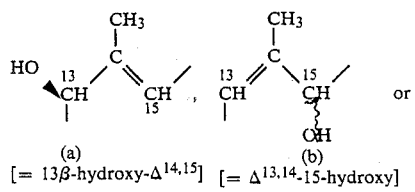

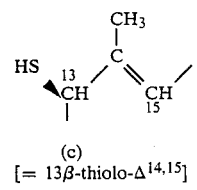

in which $R_1$ and $R_2$ are as defined for formula I. A compound of the formula II in which $R_1$ is a protective group and $R_2$ is as defined under formula I is treated with a reagent suitable for introducing or building up a 13β-thiol ester group. After this, if a free 5-hydroxy compound is desired, the $R_1$ protective group can be detached by hydrolysis.

Here and in the following text, compounds of the formula II in which A represents the group a are designated IIa, compounds containing the group b are designated IIb and compounds containing the group c are designated IIc.

The following are examples of reagents suitable for introducing the 13β-thiol ester group into compounds of the formulae IIa and IIb:

(a) thiocarboxylic acids of the formula III

RCOSH (III)

or (b) thioamides of the formula IV

RCSN(alkyl)$_2$ (IV)

in which the alkyl radicals each contain 1 to 4 carbon atoms and are preferably methyl.

Another process for the preparation of the thiol esters of the formula I consists in reacting a compound of the formula IIc with (c) an acid halide of the formula V RCOhal (V)

in which hal is halogen, preferably chlorine or bromine, or (d) an acid anhydride of the formula VI (RCO)$_2$O (VI)

the thiocarboxylic acids and thioamides being suitable for all the compounds of the formulae IIa and IIb, but being used preferably for compounds of the formula IIb, whereas acid halides and acid anhydrides are used in the case of compounds of the formula IIc.

In the formulae III–VI indicated above, R is as defined under formula I.

Compounds of the formula I in which R$_1$ is a protective group can be converted into the highly active, free 5-hydroxy derivatives (R$_1$=H) by easy detachment, for example by hydrolysis, of the protective group, and they thus have the character of intermediates. Moreover, the biological value of these compounds is not reduced by the protective group.

In general, the process is carried out in a solvent which is inert towards the reaction or in one of the reactants involved, provided that the latter are liquid. The following are examples of suitable solvents: ethers and ether-like compounds, such as dialkyl ethers (diethyl ether, diisopropyl ether, tert.-butyl methyl ether, dimethoxyethane, dioxane, tetrahydrofuran or anisole); halogenated hydrocarbons, such as chlorobenzene, methylene chloride, ethylene chloride, chloroform, carbon tetrachloride or tetrachloroethylene; or sulfoxides, such as dimethyl sulfoxide; and also aromatic or aliphatic hydrocarbons, such as benzene, toluene, xylenes, petroleum ether, ligroin or cyclohexane. In some cases it can be advantageous if the reactions are carried out under an atmosphere of a protective gas (for example argon, helium or nitrogen) and/or in absolute solvents. If desired, the end products can be purified in a customary manner, for example by washing, digestion, extraction, recrystallization or chromatography.

The reaction of compounds of the formula IIa or IIb with thiocarboxylic acids or thioamides of the formulae III or IV, respectively, is advantageously carried out in the presence of orthoesters and in the presence of catalytic amounts of a further acid. Suitable acids which can be employed for this purpose are protonic acids or Lewis acids. Examples of acids of this type are inorganic acids: hydrogen halide acids, such as hydrochloric acid, hydrobromic acid or hydroiodic acid, perchloric acid and sulfuric acid; and organic acids, such as acetic acid, trifluoroacetic acid, trichloroacetic acid, propionic acid, oxalic acid, formic acid, benzenesulfonic acid, p-toluenesulfonic acid or methanesulfonic acid; and also Lewis acids, such as BF$_3$, AlCl$_3$ or ZnCl$_2$.

p-Toluenesulfonic acid (also designated TsOH) and sulfuric acid are particularly preferred.

The orthoesters used in this reaction have the formula VII

R$_3$C(OR$_4$)$_3$ (VII)

in which R$_3$ is hydrogen or C$_1$–C$_4$-alkyl, preferably methyl, and R$_4$ is C$_1$–C$_4$-alkyl, preferably methyl or ethyl.

If thiocarboxylic acids or thioamides of the formulae III or IV, respectively, are used to prepare compounds of the formula I, the reaction temperatures are generally within the range from 0° to 150° C., preferably from 20° to 130° C.

The reaction of compounds of the formula IIc with acid halides or acid anhydrides of the formulae V and VI, respectively, is generally carried out in the above-mentioned solvents inert towards the reaction and at temperatures from −20° to +100° C., preferably from 0° to +70° C. In order absorb the acids formed thereby as a byproduct, it is advantageous to carry out the reaction in the presence of a neutralizing agent.

Suitable neutralizing agents are organic bases, for example tertiary amines, such as trialkylamines (trimethylamine, triethylamine, diisopropylmethylamine or tripropylamine), pyridine and pyridine bases (4-dimethylaminopyridine or 4-pyrrolidylaminopyridine), pyridine being preferred. The neutralizing agent is usually employed in at least an equimolar amount relative to the starting materials.

When compounds of the formula IIb are reacted with thiocarboxylic acids or thioamides of the formulae III or IV, respectively, in the presence of orthoesters of the formula VII and a catalytically active acid, compounds of the formula VIII

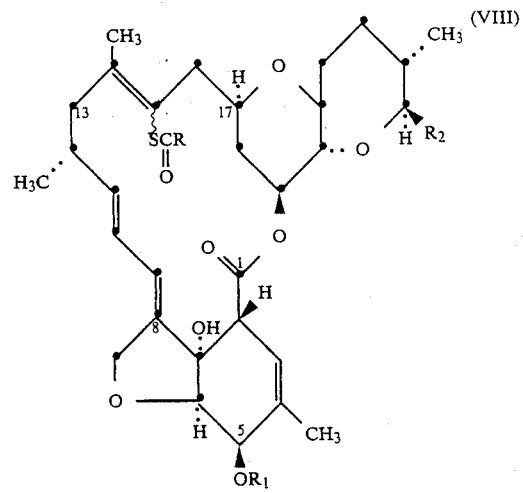

in which R$_1$, R$_2$ and R are as defined under formula I can also be formed as byproducts in addition to the compounds of the formula I.

The reaction products obtained can be separated from one another by customary methods of separation, for example fractional crystallization or chromatography. Chromatography is to be understood as meaning column, thick layer or thin layer chromatography and also, preferably, high pressure liquid chromatography over mineral supports, such as silica gel, or over organic exchange resins.

The starting compounds of the formula IIa which are required to obtain the compounds, according to the invention, of the formula I by means of the processes described herein are obtained by reacting compounds of the formula IIb with chromate, halogenochromate or dichromate ions, in particular with pyridinium dichromate $[=(Pyr)^+{}_2Cr_2O_7]$ or with pyridinium chlorochromate $[=(Pyr)^+ClCrO_3]$.

Inert, anhydrous solvents, preferably polar solvents, are used, for example dimethylformamide (=DMF). The reaction is carried out at temperatures from $-10°$ C. to $+60°$ C., preferably $+10°$ C. to $+40°$ C.

The compounds of the formula IIb are described in EP No. 147,852.

The preparation of compounds of the formula IIc can be effected by reacting a compound of the formula IIb with a halogenothionoformate of the formula IX

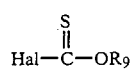

(IX)

in which $R_9$ is $C_1$-$C_{10}$-alkyl, $C_1$-$C_{10}$-halogenoalkyl or a group selected from phenyl and benzyl which group is unsubstituted or substituted by halogen, $C_1$-$C_{13}$-alkyl, $C_1$-$C_3$-halogenoalkyl, $C_1$-$C_3$-alkoxy, $C_1$-$C_3$-halogenoalkoxy, cyano and/or nitro, and by subsequently reducing the resulting product.

The reaction of compounds of the formula IIb with halogenothionoformates of the formula IX is usually carried out in the abovementioned solvents inert towards the reaction or in the halogenothionoformate of the formula IX itself. It is advantageous to carry out the reaction in the presence of a condensation agent. Suitable condensation agents are organic and inorganic bases, for example tertiary amines, such as trialkylamines (trimethylamine, triethylamine, tripropylamine etc.), pyridine and pyridine bases (4-dimethylaminopyridine, 4-pyrrolidylaminopyridine etc.), pyridine being preferred. The condensation agent is usually employed in at least an equimolar amount relative to the starting materials. The reaction temperatures in this reaction are generally $-50°$ to $+150°$ C., preferably $-20°$ to $+100°$ C. The thiol carbonates of the formula I ($R=OR_9$) formed in this reaction can be converted into the $13\beta$-mercapto compounds of the formula IIc by simple reduction, for example by means of zinc in glacial acetic acid. It is advantageous to carry out this reduction in a conventional organic solvent inert towards the reaction, at temperatures between 0° and 50° C., preferably 20° and 50° C.

All the derivatives of the formulae I, IIa, IIb and IIc in which $R_1$ is other than hydrogen ($R_1=$ an OH protective group) are prepared by acylating or silylating the 5-OH group. The introduction of the acyl group is usually effected by means of the corresponding acyl halides or acyl anhydrides and is preferably used to introduce the $R_5C(O)$-group defined initially. For silylation, it is advantageous to use a silane of the formula $Y$-$Si(R_6)(R_7)(R_8)$ in which $R_6$, $R_7$ and $R_8$ are one of the radicals mentioned initially, the term acyl halide representing an acyl chloride or acyl bromide and Y being a silyl leaving group. Examples of silyl leaving groups Y include bromide, chloride, cyanide, azide, acetamide, trifluoroacetate or trifluoromethanesulfonate. This enumeration does not constitute any limitation; those skilled in the art know further typical silyl leaving groups.

5-O-Acylation and 5-O-silylation reactions are carried out in an anhydrous medium, preferably in inert solvents and particularly preferably in aprotic solvents. The reaction proceeds advantageously within the temperature range from 0° to +80° C., preferably at $+10°$ to $+40°$ C. It is preferable to add an organic base. Examples of suitable organic bases are tertiary amines, such as triethylamine, triethylenediamine, triazole and, preferably, pyridine, imidazole or 1,8-diazabicyclo[5.4.0]undec-7ene (DBU).

The removal of these silyl and acyl radicals $R_1$ in the 5-position is effected by selective mild hydrolysis ($\rightarrow R_1=H$), for example using an arylsulfonic acid in alcoholic solution or by another method with which those skilled in the art are familiar.

The process described for the preparation of the compounds of the formula I is, in all its partial stages, a constituent of the present invention.

The compounds of the formula I are excellently suitable for controlling pests on animals and plants, including, in particular, zooparasitic ectoparasites. The latter include, from the order Acarina, especialy pests of the families Ixodidae, Dermanyssidae, Sarcoptidae and Psoroptidae; the orders Mallophaga, Siphonaptera and Anoplura (for example the family of the Haemotopinidae); and, from the order Diptera, especially pests of the families Muscidae, Calliphoridae, Oestridae, Tabanidae, Hippoboscidae and Gastrophilidae.

The compounds I can also be employed against hygiene pests, in particular those of the orders: Diptera including the families Sarcophagidae, Anophilidae and Culicidae; the order Orthoptera, the order Dictyoptera (for example the family of the Blattidae) and the order Hymenoptera (for example the family of the Formicidae).

The compounds I also possess a persistent activity in the case of phytoparasitic mites and insects. In the case of spider mites of the order Acarina, they are effective against eggs, nymphs and adults of Tetranychidae (Tetranychus spp. and Panonychus spp.).

They have a high activity in the case of sucking insects of the order Homoptera, in particular against pests of the families Aphididae, Delphacidae, Cicadellidae, Psyllidae, Coccidae, Diaspididae and Eriophydidae (for example the rust mite on citrus fruits); the orders Hemiptera, Heteroptera and Thysanoptera; and also in the case of phytophagous insects of the orders Lepidoptera, Coleoptera, Diptera and Orthoptera.

They are also suitable as a soil insecticide against pests in the soil.

The compounds of the formula I are therefore effective against all the stages of development of sucking and biting insects on crops such as cereals, cotton, rice, maize, soya, potatoes, vegetables, fruit, tobacco, hops, citrus, avocados and others.

The compounds of the formula I are also effective against plant nematodes of the species Meloidogyne, Heterodera, Pratylenchus, Ditylenchus, Radopholus, Rhizoglyphus and others.

The compounds are also effective against helminths, amongst which the endoparasitic nematodes can be the cause of serious diseases in mammals and poultry, for example in sheep, pigs, goats, cattle, horses, donkeys, dogs, cats, guinea pigs and ornamental birds. The following are typical nematodes of this indication: Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of the formula I is their effectiveness against parasites which are resistant to active substances based on benzimidazoles.

Certain of the species Nematodirus, Cooperia and Oesophagostomum attack the intestinal tract of the host animal, whereas others of the species Haemonchus and Ostertagia are parasitic in the stomach, and those of the species Dictyocaulus are parasitic in the lung tissue. Parasites of the families Filariidae and Setariidae are to be found in the internal cell tissue and the organs, for example the heart, the blood vessels, the lymph vessels and the subcutaneous tissue. Particular mention should be made here of the heart-worm of dogs, Dirofilaria immitis. The compounds of the formula I are highly effective against these parasites.

The compounds of the formula I are also suitable for the control of parasites which are pathogenic on humans, amongst which those of the species Ancylostoma, Necator, Ascaris, Strongyloides, Trichinella, Capillaria, Trichuris and Enterobius should be mentioned as typical representatives occurring in the digestive tract. The compounds of the present invention are also effective against parasites of the species Wuchereria, Brugia, Onchocerca and Loa belonging to the family of the Filariidae, which occur in the blood, in tissue and in various organs, and also against Dracunculus and parasites of the species Strongyloides and Trichinella, which infest the gastro-intestinal canal in particular.

The compounds of the formula I are employed as such or, preferably, together with the auxiliaries customary in the technology of formulation and are, therefore, processed in a known manner to give, for example, emulsion concentrates, solutions which can be atomized or diluted without further treatment, dilute emulsions, wettable powders, soluble powders, dusting agents, granules and also encapsulations in, for example, polymeric substances. The application processes, such as atomizing, nebulizing, dusting, sprinkling or watering, are selected to suit the intended aims and the given circumstances, as is also the nature of the agents.

The compounds of the formula I are administered in amounts from 0.01 to 10 mg/kg of body weight in the case of warm-blooded animals. Over closed areas cultivated for crops they are used in amounts from 10 g to 1,000 g per hectare. They are also used in pens, enclosures, stables or other places.

The formulations, i.e. the agents, formulations or compositions containing the active substance of the formula I are prepared in a known manner, for example by intimately mixing and/or grinding the active substances with extenders, for example solvents, solid carriers and, if appropriate, surface-active compounds (surfactants).

The following can be suitable as solvents: aromatic hydrocarbons, preferably the fractions from $C_8$ to $C_{12}$, for example mixed xylenes or substituted naphthalenes, phthalic acid esters, such as dibutyl or dioctyl phthalate, aliphatic hydrocarbons, such as cyclohexane or paraffins, alcohols and glycols and also ethers and esters thereof, such as ethanol, ethylene glycol or ethylene glycol monomethyl or monoethyl ether, ketones, such as cyclohexanone, strongly polar solvents, such as N-methyl-2-pyrrolidone, dimetyl sulfoxide or dimethylformamide, and optionally epoxidized vegetable oils, such as epoxidized coconut oil or soya oil or water.

The solid carriers used, for example for dusting agents and dispersible powders, are, as a rule, natural ground minerals, such as calcite, talc, kaolin, montmorillonite or attapulgite. It is also possible to add highly disperse silica or highly disperse absorbent polymers in order to improve the physical properties. Suitable particulate, adsorptive granular carriers are porous types, for example pumice stone, broken brick, sepiolite or bentonite, while examples of suitable non-sorptive carriers are calcite or sand. In addition, it is possible to use a large number of pregranulated materials of an inorganic or organic nature, such as, in particular, dolomite or comminuted plant residues.

Depending on the nature of the active substance to be formulated, suitable surface-active compounds are non-ionic, cationic and/or anionic surfactants having good emulsifying, dispersing and wetting properties. Surfactants are also to be understood as meaning mixtures of surfactants.

Suitable anionic surfactants can be so-called water-soluble soaps as well as water-soluble synthetic surfaceactive compounds.

Suitable soaps which may be mentioned are the alkali metal salts, alkaline earth metal salts or optionally substituted ammonium salts of higher fatty acids ($C_{10}$–$C_{22}$), for example the Na or K salts of oleic or stearic acid, or of natural mixtures of fatty acids, which can be obtained, for example, from coconut oil or tallow oil. Furthermore, mention should also be made of the salts of fatty acid methyltaurides.

More frequently, however, so-called synthetic surfactants are used, in particular fatty sulfonates, fatty sulfates, sulfonated benzimidazole derivatives or alkylarylsulfonates.

The fatty sulfonates or sulfates are, as a rule, in the form of alkali metal salts, alkaline earth metal salts or optionally substituted ammonium salts and contain an alkyl radical having 8 to 22 C atoms, in which connection alkyl also includes the alkyl moiety of acyl radicals, for example the Na or Ca salt of ligninsulfonic acid, of the ester of dodecylsulfuric acid or of a mixture of fatty alcohol sulfates prepared from natural fatty acids. These products also include the salts of the sulfuric acid esters and sulfonic acids of fatty alcohol/ethylene oxide adducts. The sulfonated benzimidazole derivatives preferably contain 2 sulfonic acid groups and a fatty acid radical having 8–22 C atoms. Examples of alkylarylsulfonates are the Na, Ca or triethanolamine salts of dodecylbenzenesulfonic acid, of dibutylnaphthalenesulfonic acid or of a naphthalene sulfonic acid/formaldehyde condensation product.

Furthermore, corresponding phosphates, for example salts of the phosphoric acid ester of a p-nonylphenol/-(4–14)ethylene oxide adduct, or phospholipids are also suitable.

The surfactants which are customary in the technology of formulation are described, inter alia, in the following publication:

"1985 International McCutcheon's Emulsifiers and Detergents", The Manufacturing Confectioner Publishing Co., Glen Rock, N.J., USA.

The pesticidal formulations contain, as a rule, 0.01 to 95%, in particular 0.1 to 80%, of active substance of the formula I, 5 to 99.99% of a solid or liquid additive and 0 to 25%, particularly 0.1 to 25%, of a surfactant.

Whereas concentrated agents are more likely to be preferred as commercial products, the final consumer as a rule uses dilute agents containing 1–10,000 ppm of active substance.

The present invention also relates, therefore, to pest control compositions which, in addition to customary carriers and/or distribution agents, contains, as the active substance, at least one compound of the formula I.

The agents can also contain further additives, such as stabilizers, anti-foaming agents, viscosity regulators, binders, tackifiers and fertilizers or other active substances for achieving special effects.

PREPARATION EXAMPLES

1. Preparation of starting materials and intermediates

EXAMPLE A1

Preparation of 5-O-tert.-butyldimethylsilyl-13β-hydroxymilbemycin D and of 13β-hydroxymilbemycin D (formula IIa)

A solution consisting of 286 mg (0.41 mmol) of 5-O-tert.-butyldimethylsilyl-15-hydroxy-$\Delta^{13,24}$-milbemycin D and 209 mg (0.56 mmol) of pyridinium dichromate (PDC) in 3 ml of dimethylformamide (DMF) is stirred at room temperature for 30 minutes. 1 ml of isopropanol is then added and the mixture is stirred for a further 5 minutes and is then diluted with 50 ml of ether. After a further 10 minutes the mixture is filtered through silica gel and concentrated. Purifying the crude product by chromatography over 20 g of silica gel (1:2 ether/hexane) gives 165 mg (57%) of 5-O-t-butyldimethyl- silyl-13β-hydroxymilbemycin D.

$^1$H-NMR (300 MHz; CDCl$_3$; TMS): 1.59 ppm (br. s) (C$_{14}$CH$_3$) 3.70 ppm (d; J=10 Hz) (C$_{13}$H).

105 mg (0.153 mmol) of the compound thus obtained are stirred with 1 ml of a 1% solution of p-toluenesulfonic acid in methanol at room temperature for 1 hour. The mixture is diluted with 20 ml of ether, filtered through silica gel and concentrated. The residue is chromatographed over approx. 10 g of silica gel (1:4 acetone/methylene dichloride), and 73 mg (83%) of 13β-hydroxymilbemycin D are obtained.

$^1$H-NMR (300 MHz; CDCl$_3$; TMS): 1.58 ppm (br.s) (C$_{14}$CH$_3$) 3.71 ppm (d; J=10 Hz) (C$_{13}$H).

EXAMPLE A2

Preparation of 13β-mercaptomilbemycin D and of 5-O-tert.-butyldimethylsilyl-13β-mercaptomilbemycin D (a) 0.1 ml (157 mg, 0.689 mmol) of trichloroethyl chlorothionoformate are added dropwise, under argon, at $-10°$ C. and with stirring, to a solution of 209 mg (0.305 mmol) of 5-O-tert.-butyldimethylsilyl-15-hydroxy-$\Delta^{13,14}$-milbemycin D and 0.012 ml (120 mg, 1.52 mmol) of pyridine in 3 ml of methylene dichloride. After being stirred for 1 hour at room temperature, the mixture is worked up with 5% aqueous NaHCO$_3$ solution and diethyl ether. Chromatographing the crude product [20 g of silica gel/eluant 1:4 ethyl acetate/hexane] gives 282 mg of 5-O-tert.-butyldimethylsilyl-13β-trichloroethoxycarbonylthiomilbemycin D, which is still impure to some extent.

A suspension of 320 mg (4.9 mmol) of zinc powder in a solution of 227 mg of this crude product in 0.5 ml of diethyl ether, 2 ml of 90% aqueous acetic acid and 3 drops of HCl (1 M) is stirred under argon at room temperature for 16 hours. The mixture is diluted with diethyl ether, filtered through kieselguhr, dried by means of MgSO$_4$ and concentrated. Chromatographing the crude product [20 g of silica gel/eluant 12:88 ethyl acetate/hexane]gives 72 mg (40%) of 5-O-tert.-butyl-dimethylsilyl-13β-mercaptomilbemycin D.

(b) This purified product is stirred with 2 ml of a 1% solution of p-toluenesulfonic acid in methanol for 2 hours at room temperature. After being worked up with 5% aqueous NaHCO$_3$ solution and diethyl ether, the crude product is chromatographed [20 g of silica gel-/eluant 2:3 ethyl acetate/hexane]. This gives 54 mg (89%) of 13β-mercaptomilbemycin D having the following spectroscopic data:

$^1$H-NMR (300 MHz; CDCl$_3$; TMS): 1.61 ppm (s) (C$_{14}$CH$_3$) 1.87 ppm (s) (C$_4$CH$_3$) 3.31 ppm (dd; J=5.4 and 10.9), (C$_{13}$H)

Mass spectrum m/e: 588 (M$^+$, C$_{33}$H$_{48}$O$_7$S) 460, 309, 277, 209, 181.

EXAMPLE A3

Preparation of 5-O-tert.-butyldimethylsilyl-13β-hydroxymilbemycin A$_4$

A solution consisting of 1.06 g (1.59 mmol) of 5-O-tert.-butyldimethylsilyl-15-hydroxy-$\Delta^{13,14}$-milbemycin A$_4$ and 383 mg (1.02 mmol) of pyridinium dichromate (PDC) in 5 ml of dimethylformamide (DMF) is stirred at room temperature for 30 minutes. 1 ml of isopropanol is then added and the mixture is stirred for a further 5 minutes and is then diluted with 50 ml of ether. After a further 10 minutes the mixture is filtered through silica gel and concentrated. Purifying the crude product by chromatography over 20 g of silica gel (1:2 ether/hexane) gives 625 mg (59%) of 5-O-t-butyldimethylsilyl-13β-hydroxymilbemycin A$_4$.

$^1$H-NMR (300 MHz; CDCl$_3$; TMS): 0.98 ppm (t; J=7 Hz) (CH$_3$CH$_2$) 1.95 ppm (br. s) (C$_{14}$CH$_3$) 3.69 ppm (d; J=9 Hz) (C$_{13}$H).

EXAMPLE A4

Preparation of 5-O-tert.-butyldimethylsilyl-13β-mercaptomilbemycin A$_4$ (a) 0.13 ml (205 mg, 0.9 mmol) of trichloroethyl chlorothionoformate are added dropwise, under argon, at $-10°$ C. and with stirring, to a solution of 100 mg (0.15 mmol) of 5-O-tert.-butyldimethylsilyl-15-hydroxy-$\Delta^{13, 14}$-milbemycin A$_4$ and 0.060 ml (59 mg, 0.75 mmol) of pyridine in 3 ml of methylene dichloride. After being stirred for 30 minutes at room temperature, the mixture is worked up with 5% aqueous NaHCO$_3$ solution and diethyl ether. Chromatographing the crude product [20 g of silica gel/eluant 1:12 ethyl acetate/hexane] gives 40 mg of 5-O-tert.-butyldimethylsilyl-13β-trichloroethoxycarbonylthiomilbemycin A$_4$.

$^1$H-NMR (300 MHz; CDCl$_3$; TMS): 3.82 ppm (d; J=10 Hz) (C$_{13}$H) 4.75 ppm (d; J=14 Hz) and 4.86 (d; J=14 Hz) (Cl$_3$CCH$_2$)

Mass spectrum (FD) m/e: 862 (M$^+$, C$_{41}$H$_{61}$Cl$_3$O$_9$SSi).

(b) A solution of 2.9 g (3.36 mmol) of 5-O-tert.-butyldimethylsilyl-13β-trichloroethoxycarbonylthiomilbemycin A$_4$ in 40 ml of tetrahydrofuran is vigorously stirred for 5 hours with 1.05 g (16.1 mmol) of zinc and 20 ml of saturated aqueous NH$_4$Cl. The mixture is worked up with water and diethyl ether. Chromatographing the crude product [silica gel/eluant 1:9 ethyl acetate/hexane] gives 2.46 g of 5-O-tert.-butyldimethylsilyl-13β-mercaptomilbemycin A⁴.

$^1$H-NMR (300 MHz; CDCl$_3$; TMS): 3.29 ppm (dd; J=10 and 5 Hz) (C$_{13}$H)

Mass spectrum m/e: 688 (M+, C$_{38}$H$_{60}$O$_7$SSi).

EXAMPLE A5

Preparation of 5-O-tert.-butyldimethylsilyl-13β-mercaptomilbemycin A$_3$

5-O-tert.-Butyldimethylsilyl-13β-mercaptomilbemycin A$_3$ is prepared analogously to Example A4.

(a) 5-O-tert.-Butyldimethylsilyl-13β-trichloroethoxycarbonylthiomilbemycin A$_3$:

$^1$H-NMR (300 MHz; CDCl$_3$; TMS): 3.84 ppm (d; J=10 Hz) (C$_{13}$H) 4.76 ppm (d; J=14 Hz) and 4.87 (d; J=14 Hz) (Cl$_3$CCH$_2$)

Mass spectrum (FD) m/e: 848 (M+, C$_{40}$H$_{59}$Cl$_3$O$_9$SSi).

(b) 5-O-tert.-Butyldimethylsilyl-13β-mercaptomilbemycin A$_3$:

$^1$H-NMR (300 MHz; CDCl$_3$; TMS): 3.29 ppm (dd; J=10 and 5 Hz) (C$_{13}$H)

Mass spectrum m/e=674 (M+, C$_{37}$H$_{58}$O$_7$SSi).

2. Preparation of end products

EXAMPLE H1

Preparation of 13β-pivaloylthiomilbemycin A$_4$

A solution of 280 mg (0.416 mmol) of 5-O-tert.-butyldimethylsilyl-15-hydroxy-Δ$^{13,14}$-milbemycin A$_4$, 0.4 ml of trimethyl orthoacetate and 0.4 ml of thiopivalic acid in 4 ml of toluene is heated at 60° C. for 6 hours. The mixture is worked up with diethyl ether and 5% aqueous NaHCO$_3$ solution. Chromatography over silica gel (1:6 ethyl acetate/hexane) gives 61 mg of 5-O-tert.-butyldimethylsilyl-13β-pivaloylthiomilbemycin A$_4$.

This material is treated with 2 ml of a 40% aqueous solution of HF and acetonitrile (5:95) for 2 hours at room temperature. Working up in diethyl ether with 5% aqueous NaHCO$_3$ solution and chromatography over silica gel (1:2 ethyl acetate/hexane) gives 21 mg of 13β-pivaloylthiomilbemycin A$_4$.

$^1$H-NMR (250 MHz; CDCl$_3$; TMS): 1.25 ppm (s) [(CH$_3$)$_3$C] 3.97 ppm (d) (J=10 Hz) (C$_{13}$H) 4.01 ppm (d) (J=6 Hz) (C$_6$H)

EXAMPLE H2

Preparation of 13β-acetylthiomilbemycin A$_4$

13β-Acetylthiomilbemycin A$_4$ is prepared analogously to Example H1.

$^1$H-NMR (300 MHz; CDCl$_3$; TMS): 2.32 ppm (s) (CH$_3$COS) 3.96 ppm (d, J=6 Hz) (C$_6$H) 4.03 ppm (d, J=10 Hz) (C$_{13}$H).

EXAMPLE H3

Preparation of 5-O-tert.-butyldimethylsilyl-13β-(2-n-propyl-n-valeroylthio)-milbemycin A$_4$ and of 13β-(2-n-propyl-n-valeroylthio)-milbemycin A$_4$ (a) 0.2 ml of 2-n-propyl-n-valeroyl chloride are added, under argon, at 0° C. and with stirring, to a solution of 110 mg (0.154 mmol) of 5-O-tert.-butyldimethylsily--13β-mercaptomilbemycin A$_4$ in 5 ml of absolute chloroform and 2 ml of pyridine. After being stirred for 7 hours at room temperature, the mixture is worked up with ice-cold, dilute aqueous HCl, dilute aqueous NaHCO$_3$ solution and diethyl ether. Chromatographing the crude product [10 g of silica gel/eluant 1:5 ethyl acetate/hexane] gives 92 mg of 5-O-tert.-butyldimethylsilyl-13β-(2-n-propyl-n-valeroylthio)-milbemycin A$_4$.

(b) This purified product is stirred with 1 ml of a 1% solution of p-toluenesulfonic acid in methanol for 3 hours at room temperature. The mixture is worked up with 5% aqueous NaHCO$_3$ solution and diethyl ether, and the crude product is chromatographed [10 g of silica gel/eluant 1:3 ethyl acetate/hexane]. This gives 49 mg of 13β-(2-n-propyl-n-valeroylthio)-milbemycin A$_4$ having the following spectroscopic data:

$^1$H-NMR (300 MHz; CDCl$_3$; TMS): 3.95 ppm (d, J=6 Hz) (C$_6$H) 3.97 ppm (d, J=10 Hz) (C$_{13}$H)

MS (FD) m/e: 700 (M+, C$_{40}$H$_{60}$O$_8$S).

The compounds listed in the following examples H4 to H16 are prepared analogously to the process described in Example H3:

EXAMPLE H4

13β-Acetylthiomilbemycin A$_4$

MS (FD) m/e: 616 (M+, C$_{34}$H$_{48}$O$_8$S).

EXAMPLE H5

13β-(2-trifluoromethylbenzoyl)-milbemycin A$_4$ $^1$H-NMR (300 MHz; CDCl$_3$; TMS): 3.97 ppm (d, J=6 Hz) (C$_6$H) 4.21 ppm (d, J=10 Hz) (C$_{13}$H) 7.48–7.76 ppm (m) (4 aromatic H)

MS (FD) m/e: 746 (M+, C$_{40}$H$_{49}$O$_8$SF$_3$).

EXAMPLE H6

13β-[(R/S)-2-phenylpropionylthio)-milbemycin A$_4$; mixture of diastereomers $^1$H-NMR (300 MHz; CDCl$_3$; TMS): 3.75 and 3.83 ppm (2q, J=6 hz) (C'$_2$H) 3.82 and 3.93 ppm (2d, J=6 Hz) (C$_6$H) 3.81 and 3.94 ppm (2d, J=10 Hz) (C$_{13}$H) 7.11–7.37 ppm (m) (5 aromatic H).

EXAMPLE H7

13β-(2,2-dimethylbutyrylthio)-milbemycin A$_4$ $^1$H-NMR (300 MHz; CDCl$_3$; TMS): 3.91 ppm (d, J=10 Hz) (C$_{13}$H) 3.95 ppm (d, J=6 Hz) (C$_6$H)

MS (FD) m/e: 672 (M+, C$_{38}$H$_{56}$O$_8$S).

EXAMPLE H8

13β-(3-chloro-2,2-dimethylpropionylthio)-milbemycin A$_4$ $^1$H-NMR (300 MHz; CDCl$_3$; TMS): 3.93 ppm (d, J=10 Hz) (C$_{13}$H) 3.96 ppm (d, J=6 Hz) (C$_6$H) 3.60 ppm (AB system, J=13 Hz; A fraction: 3.57 ppm, B fraction: 3.63 ppm) (CH$_2$Cl).

EXAMPLE H9

13β-(2-methyl-2-phenylpropionylthio)-milbemycin A$_4$ $^1$H-NMR (300 MHz; CDCl$_3$; TMS): 3.89 ppm (d, J=11 Hz) (C$_{13}$H) 3.93 ppm (d, J=6 Hz) (C$_6$H) 7.19–7.37 (m) (5 aromatic H).

EXAMPLE H10

13β-(3-fluoro-2,2-dimethylpropionylthio)-milbemycin A$_4$ $^1$H-NMR (300 MHz; CDCl$_3$; TMS): 3.94 ppm (d, J=6 Hz (C$_6$H) 3.98 ppm (d, J=10 Hz) (C$_{13}$H) 4.37 ppm (d, J=47 Hz) (CH$_2$F)
MS (FD) m/e: 676 (M+, C$_{37}$H$_{53}$FO$_8$S).

EXAMPLE 11

13β-methoxyacetylthiomilbemycin A$_4$ $^1$H-NMR (300 MHz; CDCl$_3$; TMS): 3.94 ppm (d, J=6 Hz) (C$_6$H) 4.03 ppm (d, J=10 Hz) (C$_{13}$H) 3.45 ppm (s)(CH$_3$OCH$_2$) 4.04 ppm (s)(CH$_3$OCH$_2$)
MS (FD) m/e: 646 (M+, C$_{35}$H$_{50}$O$_9$S).

EXAMPLE H12

13β-[(S)-2-phenylpropionylthio]-milbemycin A$_4$ $^1$H-NMR (300 MHz; CDCl$_3$; TMS): 3.83 ppm (q, J=6 Hz) (C'$_2$H) 3.93 ppm (d, J=6 Hz) (C$_6$H) 3.94 ppm (d, J=10 Hz) (C$_{13}$H) 7.18–7.37 (m) (5 aromatic H).

EXAMPLE H13

13β-[(R)-2-phenylpropionylthio]-milbemycin A$_4$ $^1$H-NMR (300 MHz; CDCl$_3$; TMS): 3.75 ppm (q, J=6 Hz) (C'$_2$H) 3.81 ppm (d, J=10 Hz) (C$_{13}$H) 3.82 ppm (d, J=6 Hz) (C$_6$H) 7.11–7.26 ppm (m) (5 aromatic H).

EXAMPLE H14

13β-[2,3-(difluoromethylenedioxy)-benzoylthio]milbemycin A$_4$ $^1$H-NMR (300 MHz; CDCl$_3$; TMS): 3.95 ppm (d, J=6 Hz) (C$_6$H) 4.25 ppm (d, J=10 Hz) (C$_{13}$H) 7.12 ppm (dd, J=8 and 8 Hz) (C'$_5$H) 7.23 ppm (dd, J=2 and 8 Hz) (C'$_4$H) 7.63 ppm (dd, J=2 and 8 Hz) (C'$_6$H).

EXAMPLE H15

13β-chloroacetylthiomilbemycin A$_4$ $^1$H-NMR (300 MHz; CDCl$_3$; TMS): 3.94 ppm (d, J=6 Hz) (C$_6$H) 4.02 ppm (d, J=10 Hz) (C$_{13}$H) 4.03 and 4.16 (2s) (CH$_2$Cl).

EXAMPLE H16

13β-pivaloylthiomilbemycin A$_3$ $^1$H-NMR (300 MHz; CDCl$_3$; TMS): 1.24 ppm (s) [(CH$_3$)$_3$C]3.97 ppm (d, J=10 Hz) (C$_{13}$H) 4.03 ppm (d, J=6 Hz) (C$_6$H).

The compounds of the formula I mentioned below, together with compounds from the preceding examples, are also prepared analogously to the procedures described:

TABLE 1

Typical representatives of compounds of the formula 1 in which R$_1$ is hydrogen.

| Compound No. | R$_2$ | R |
|---|---|---|
| 1.1 | CH$_3$ | H |
| 1.2 | C$_2$H$_5$ | H |
| 1.3 | C$_3$H$_7$—iso | H |
| 1.4 | C$_4$H$_9$—sec | H |
| 1.5 | CH$_3$ | CH$_3$ |
| 1.6 | C$_2$H$_5$ | CH$_3$ |
| 1.7 | C$_3$H$_7$—iso | CH$_3$ |
| 1.8 | C$_4$H$_9$—sec | CH$_3$ |
| 1.9 | CH$_3$ | C(CH$_3$)$_3$ |
| 1.10 | C$_2$H$_5$ | C(CH$_3$)$_3$ |
| 1.11 | C$_3$H$_7$—iso | C(CH$_3$)$_3$ |
| 1.12 | C$_4$H$_9$—sec | C(CH$_3$)$_3$ |
| 1.13 | CH$_3$ | CH$_3$OCH$_2$ |
| 1.14 | C$_2$H$_5$ | CH$_3$OCH$_2$ |
| 1.15 | C$_3$H$_7$—iso | CH$_3$OCH$_2$ |
| 1.16 | C$_4$H$_9$—sec | CH$_3$OCH$_2$ |
| 1.17 | CH$_3$ | CH$_3$OC(CH$_3$)$_2$ |
| 1.18 | C$_2$H$_5$ | CH$_3$OC(CH$_3$)$_2$ |
| 1.19 | C$_3$H$_7$—iso | CH$_3$OC(CH$_3$)$_2$ |
| 1.20 | C$_4$H$_9$—sec | CH$_3$OC(CH$_3$)$_2$ |
| 1.21 | CH$_3$ | (CH$_3$)$_2$CH |
| 1.22 | C$_2$H$_5$ | (CH$_3$)$_2$CH |
| 1.23 | C$_3$H$_7$—iso | (CH$_3$)$_2$CH |
| 1.24 | C$_4$H$_9$—sec | (CH$_3$)$_2$CH |
| 1.25 | CH$_3$ | CCl$_3$ |
| 1.26 | C$_2$H$_5$ | CCl$_3$ |
| 1.27 | C$_3$H$_7$—iso | CCl$_3$ |
| 1.28 | C$_4$H$_9$—sec | CCl$_3$ |
| 1.29 | CH$_3$ | CF$_3$ |
| 1.30 | C$_2$H$_5$ | CF$_3$ |
| 1.31 | C$_3$H$_7$—iso | CF$_3$CHCl |
| 1.32 | C$_4$H$_9$—sec | CF$_3$ |
| 1.33 | CH$_3$ | C(Cl$_3$)CHCl |
| 1.34 | C$_2$H$_5$ | C(Cl$_3$)CHCl |
| 1.35 | C$_3$H$_7$—iso | CF$_3$CH$_2$ |
| 1.36 | C$_4$H$_4$—sec | C(Cl$_3$)CHCl |
| 1.37 | CH$_3$ | ClCH$_2$CH$_2$CH$_2$ |
| 1.38 | C$_2$H$_5$ | ClCH$_2$CH$_2$CH$_2$ |
| 1.39 | C$_3$H$_7$—iso | ClCH$_2$CH$_2$CH$_2$ |
| 1.40 | C$_4$H$_9$—sec | ClCH$_2$CH$_2$CH$_2$ |
| 1.41 | CH$_3$ | CH$_2$=CH |
| 1.42 | C$_2$H$_5$ | CH$_2$=CH |
| 1.43 | C$_3$H$_7$—iso | CH$_2$=CH |
| 1.44 | C$_4$H$_9$—sec | CH$_2$=CH |
| 1.45 | CH$_3$ | CH$_2$=CH—CH$_2$ |
| 1.46 | C$_2$H$_5$ | CH$_2$=CH—CH$_2$ |
| 1.47 | C$_3$H$_7$—iso | CH$_2$=CH—CH$_2$ |
| 1.48 | C$_4$H$_9$—sec | CH$_2$=CH—CH$_2$ |
| 1.49 | CH$_3$ | CH≡C—CH$_2$ |
| 1.50 | C$_2$H$_5$ | CH≡C—CH$_2$ |
| 1.51 | C$_3$H$_7$—iso | CH≡C—CH$_2$ |
| 1.52 | C$_4$H$_9$—sec | CH≡C—CH$_2$ |
| 1.53 | CH$_3$ | (CH$_3$)$_2$C=CH |
| 1.54 | C$_2$H$_5$ | (CH$_3$)$_2$C=CH |
| 1.55 | C$_3$H$_7$—iso | (CH$_3$)$_2$C=CH |
| 1.56 | C$_4$H$_9$—sec | (CH$_3$)$_2$C=CH |
| 1.57 | CH$_3$ | (Cl)$_2$C=C(Cl) |
| 1.58 | C$_2$H$_5$ | (Cl)$_2$C=C(Cl) |
| 1.59 | C$_3$H$_7$—iso | (Cl)$_2$C=C(Cl) |
| 1.60 | C$_4$H$_9$—sec | (Cl)$_2$C=C(Cl) |
| 1.61 | CH$_3$ | CF$_3$CCl$_2$ |
| 1.62 | C$_2$H$_5$ | CF$_3$CCl$_2$ |
| 1.63 | C$_3$H$_7$—iso | CF$_3$CCl$_2$ |
| 1.64 | C$_4$H$_9$—sec | CF$_3$CCl$_2$ |
| 1.65 | CH$_3$ | Cyclopropyl |
| 1.66 | C$_2$H$_5$ | Cyclopropyl |
| 1.67 | C$_3$H$_7$—iso | Cyclopropyl |
| 1.68 | C$_4$H$_9$—sec | Cyclopropyl |
| 1.69 | CH$_3$ | 2,2-Dimethylcyclopropyl |
| 1.70 | C$_2$H$_5$ | 2,2-Dimethylcyclopropyl |
| 1.71 | C$_3$H$_7$—iso | 2,2-Dimethylcyclopropyl |
| 1.72 | C$_4$H$_9$—sec | 2,2-Dimethylcyclopropyl |
| 1.73 | CH$_3$ | 2,2-Dimethyl-3-(2,2-dichlorovinyl)-cyclopropyl |
| 1.74 | C$_2$H$_5$ | 2,2-Dimethyl-3-(2,2-dichlorovinyl)-cyclopropyl |
| 1.75 | C$_3$H$_7$—iso | 2,2-Dimethyl-3-(2,2-dichlorovinyl)-cyclopropyl |
| 1.76 | C$_4$H$_9$—sec | 2,2-Dimethyl-3-(2,2-di- |

TABLE 1-continued

Typical representatives of compounds of the formula 1 in which $R_1$ is hydrogen.

| Compound No. | $R_2$ | R |
|---|---|---|
| | | chlorovinyl)-cyclopropyl |
| 1.77 | $CH_3$ | Cyclobutyl |
| 1.78 | $C_2H_5$ | Cyclobutyl |
| 1.79 | $C_3H_7$—iso | Cyclobutyl |
| 1.80 | $C_4H_9$—sec | Cyclobutyl |
| 1.81 | $CH_3$ | Cyclohexyl |
| 1.82 | $C_2H_5$ | Cyclohexyl |
| 1.83 | $C_3H_7$—iso | Cyclohexyl |
| 1.84 | $C_4H_9$—sec | Cyclohexyl |
| 1.85 | $CH_3$ | Phenyl |
| 1.86 | $C_2H_5$ | Phenyl |
| 1.87 | $C_3H_7$—iso | Phenyl |
| 1.88 | $C_4H_9$—sec | Phenyl |
| 1.89 | $CH_3$ | p-chlorophenyl |
| 1.90 | $C_2H_5$ | p-chlorophenyl |
| 1.91 | $C_3H_7$—iso | p-chlorophenyl |
| 1.92 | $C_4H_9$—sec | p-chlorophenyl |
| 1.93 | $CH_3$ | p-Tolyl |
| 1.94 | $C_2H_5$ | p-Tolyl |
| 1.95 | $C_3H_7$—iso | p-Tolyl |
| 1 95 | $C_3H_7$—iso | p-Tolyl |
| 1.96 | $C_4H_9$—sec | p-Tolyl |
| 1.97 | $CH_3$ | p-Nitrophenyl |
| 1.98 | $C_2H_5$ | p-Nitrophenyl |
| 1.99 | $C_3H_7$—iso | p-Nitrophenyl |
| 2.00 | $C_4H_9$—sec | p-Nitrophenyl |
| 2.1 | $CH_3$ | n-Hexyl |
| 2.2 | $C_2H_5$ | n-Hexyl |
| 2.3 | $C_3H_7$—iso | n-Hexyl |
| 2.4 | $C_4H_9$—sec | n-Hexyl |
| 2.5 | $CH_3$ | $ClCH_2C(CH_3)_2$ |
| 2.6 | $C_2H_5$ | $ClCH_2C(CH_3)_2$ |
| 2.7 | $C_3H_7$—iso | $ClCH_2C(CH_3)_2$ |
| 2.8 | $C_4H_9$—sec | $ClCH_2C(CH_3)_2$ |
| 2.9 | $CH_3$ | 1-Methylcyclopropyl |
| 2.10 | $C_2H_5$ | 1-Methylcyclopropyl |
| 2.11 | $C_3H_7$—iso | 1-Methylcyclopropyl |
| 2.12 | $C_4H_9$—sec | 1-Methylcyclopropyl |
| 2.13 | $CH_3$ | Adamantyl |
| 2.14 | $C_2H_5$ | Adamantyl |
| 2.15 | $C_3H_7$—iso | Adamantyl |
| 2.16 | $C_4H_9$—sec | Adamantyl |
| 2.17 | $C_2H_5$ | p-Fluorophenoxymethyl |
| 2.18 | $C_2H_5$ | $ClC(CH_3)_2$ |
| 2.19 | $C_2H_5$ | $CH_3CCl_2$ |
| 2.20 | $C_2H_5$ | $CH_3CH_2C(CH_3)_2$ |
| 2.21 | $C_2H_5$ | $C(CH_3)_3CH_2$ |
| 2.22 | $C_2H_5$ | $C(CH_3)_3C(CH_3)_2$ |
| 2.23 | $C_2H_5$ | $ClCH_2$ |
| 2.24 | $C_2H_5$ | $CF_3CH_2$ |
| 2.25 | $C_2H_5$ | 1-Methylcyclobutyl |
| 2.26 | $C_2H_5$ | 1-Methylcyclopentyl |
| 2.27 | $C_2H_5$ | $FCH_2C(CH_3)_2$ |
| 2.28 | $C_2H_5$ | $CH_2=C(CH_3)$ |
| 2.29 | $C_2H_5$ | $ClCH_2CH_2$ |
| 2.30 | $C_2H_5$ | p-(tert.-$C_4H_9$)-phenyl |
| 2.31 | $C_2H_5$ | $CH_3CH_2CH_2$ |
| 2.32 | $C_2H_5$ | $CH_3CH_2$ |
| 2.33 | $C_2H_5$ | o-(Trifluoromethyl)-phenyl |
| 2.34 | $C_2H_5$ | (R/S)-α-Methylbenzyl |
| 2.35 | $C_2H_5$ | (S)-α-Methylbenzyl |
| 2.36 | $C_2H_5$ | (R)-α-Methylbenzyl |
| 2.37 | $C_2H_5$ | α,α-Dimethylbenzyl |
| 2.38 | $C_2H_5$ | $(CH_3CH_2CH_2)_2CH$ |
| 2.39 | $C_2H_5$ | 2,3-(Difluoromethylene-dioxy)-phenyl |

The contents of the table have the character of an illustration and do not constitute any Limitation.

Examples of formuLations of active substance of the formuLa I (%—percent by weight)

| F1. Wettable powders | (a) | (b) | (c) |
|---|---|---|---|
| Active substance from Table 1 | 25% | 50% | 75% |
| Na Ligninsulfonate | 5% | 5% | — |
| Na Laurylsulfate | 3% | — | 5% |
| Na diisobutylnaphthalene-sulfonate | — | 6% | 10% |
| Octylphenol polyethylene glycol ether (7-8 mol of EO) | | 2% | |
| Highly disperse silica | 5% | 10% | 10% |
| Kaolin | 62% | 27% | — |

The active substance is thoroughly mixed with the additives, and the mixture is thoroughly ground in a suitable mill. This gives wettable powders which can be diluted with water to give suspensions of any desired concentration.

| F2. Emulsion concentrate | |
|---|---|
| Active substance from Table 1 | 10% |
| Octylphenyl polyethylene glycol ether (4-5 mol of EO) | 3% |
| Ca dodecylbenzenesulfonate | 3% |
| Castor oil polyglycol ether (36 mol of EO) | 4% |
| Cyclohexanone | 30% |
| Mixed xylenes | 50% |

Emulsions of any desired concentration can be prepared from this concentrate by dilution with water.

| F3. Dusts | (a) | (b) |
|---|---|---|
| Active substance from Table 1 | 5% | 8% |
| Talc | 95% | — |
| Kaolin | — | 92% |

Ready-to-use dusts are obtained by mixing the active substance with the carrier and grinding the mixture on a suitable mill.

| F4. Extruder granules | |
|---|---|
| Active substance from Table 1 | 10% |
| Na Ligninsulfonate | 2% |
| Carboxymethylcellulose | 1% |
| Kaolin | 87% |

The active substance is mixed with the additives, and the mixture is ground and moistened with water. This mixture is extruded and then dried in a stream of air.

| F5. Tablets, pellets | |
|---|---|
| I Active substance from Table 1 | 33.0% |
| Methylcellulose | 0.80% |
| Highly disperse silica | 0.80% |
| Maize starch | 8.40% |

The methylcellulose is stirred into water and allowed to swell; the silica is stirred into the swollen mass to form a homogeneous suspension. The active substance and the maize starch are mixed. The aqueous suspension is worked into this mixture and kneaded to form a paste. This composition is granulated through a sieve (mesh width 12M) and is then dried.

| | |
|---|---|
| II Crystalline lactose | 22.50% |
| Maize starch | 17.00% |
| Microcrystalline cellulose | 16.50% |
| Magnesium stearate | 1.00% |

All 4 adjuncts are thoroughly mixed; phases I and II are mixed and compressed to give tablets or pellets.

When compounds of the formula I or corresponding agents are used for the control of endoparasitic nematodes, cestodes and trematodes in domestic animals and productive livestock, such as cattle, sheep, goats, cats and dogs, the compounds for agents can be administered to the animals either as an individual dose or on a repeated basis, the individual doses being preferably between 0.1 and 10 mg per kg of body weight, depending on the species of animal. In some cases a better action is achieved by a protracted administration or it is possible to manage with lower total doses. The active substance or the agents containing it can also be added to the feed or the drinks. The combinations of active substances are preferably present in the prepared feed in a concentration of 0.005 to 0.1% by weight. The agents can be administered to the animals perorally in the form of solutions, emulsions, suspensions, powder, tablets, pellets, boluses or capsules. Insofar as the physical and toxicological properties of solutions or emulsions permit, the compounds of the formula I or the agents containing them can also be administered to the animals, for example, by subcutaneous injection or intraruminally or can be applied to the body of the animals by the pour-on method. It is also possible to administer the active substance to the animals by means of lickstones (salt) or molasses blocks.

BIOLOGICAL EXAMPLES

B1. Action against $L_1$ larvae of *Lucilia sericata*

1 ml portions of an aqueous suspension of the active substance to be tested are mixed with 3 ml of a special larval culture medium at approx. 50° C. in such a way that a homogenate containing either 250 ppm or 100 ppm of active substance is formed. Approx. 30 Lucilia larvae ($L_1$) are put into each test tube sample. The mortality rate is determined after 4 days. At 250 ppm, compounds of the formula I achieve a 100% action. This effect can also be achieved at a lower dosage with, for example, compounds 1.6, 2.6, 2.20, 2.34, 2.37 and 2.38, and these compounds are also at least of equal effectiveness against Lucilia cuprina.

B2 Acaricidal action against *Boophilus microplus* (Biarra strain)

An adhesive strip is fastened horizontally on a PVC sheet in such a way that 10 female ticks of Boophilus microplus (Biarra strain), fully sucked with blood, can be glued thereto on their backs, side by side in a row. Each tick is injected by means of a hypodermic needle with 1 μl of a liquid which is a 1:1 mixture of polyethylene glycol and acetone and in which a specific amount of active substance, either 1, 0.5, 0.1 or 0.01 μg per tick, has been dissolved. Control animals receive an injection of the corresponding mixture with no active substance. After treatment, the animals are kept under normal conditions in an insectarium at approx. 28° C. and 80% relative humidity until oviposition takes place and the larvae have hatched out from the eggs of the control animals.

The activity of a substance tested is determined by means of the $IR_{90}$, i.e. the dose of active substance is determined at which, after 30 days, 9 out of 10 female ticks (=90%) lay eggs which are not capable of hatching.

Compounds of the formulae I achieve an $IR^{90}$ of 0.5 μg.

B3. Test on sheep infested with nematodes (*Haemonchus contortus* and *Trichostrongylus colubriformis*)

The active substance, formulated as a suspension, is administered by means of a probang or by injection into the rumin of a sheep which has been artificially infested with *Haemonchus contortus* and *Trichostrongylus colubriformis*. 1 to 3 animals are used per dose. Each sheep is treated only once with a single dose, this being 0.5 mg/kg of body weight. Evaluation is carried out by comparing the number of worm eggs excreted in the faeces of other sheep before and after treatment.

Sheep which have been infested at the same time and in the same manner, but have not been treated, are used as a control. In comparison with untreated, but infested, comparison groups, sheep which are treated with one of the compounds of the formula I at 0.5 mg/kg exhibit no attack by nematodes (complete reduction of worm eggs in the faeces). Lowering the dose further to ranges between 0.1 and 0.2 mg/kg gives a reduction of over 50% for compounds 1.6, 1.10 and 2.27, for example, and a reduction of over 90% for compounds 1.14 and 2.34.

B4. Larvicidal action against *Aedes aegypti*

Sufficient of a 0.1% acetone solution of the active substance to give concentrations of either 10 ppm, 3.3 ppm and 1.6 ppm is pipetted onto the surface of 150 ml of water, contained in a vessel. After the acetone has evaporated, the vessel is charged with approx. 30–40 Aedes larvae 3 days old. The mortality is checked after 1, 2 and 5 days.

Compounds of the formulae I effect complete destruction of all the larvae in this test at a concentration of 1.6 ppm and after only one day.

B5. Miticidal action against *Dermanyssus gallinae*

2 to 3 ml of a test solution (100, 10, 1 and 0.1 ppm of active substance) are put into a glass vessel open at the top, and approx. 200 mites in various stages of development are put into this vessel. The glass vessel is closed with a plug of cottonwool and shaken uniformly for 10 minutes until the mites are completely wetted. The vessel is then turned upside down until the excess test solution has been absorbed by the cottonwool. The vessel is turned over again and the treated ticks are observed under laboratory conditions for three days in order to evaluate the effectiveness of the test substances, the mortality being used as a criterion of effectiveness.

The compounds of the formula I exhibit a good action in this test. Thus a 100% action is obtained, for example, with compounds 1.6, 2.6, 2.20, 2.27, 2.34, 2.37 and 2.38 at 100 ppm.

What is claimed is:
1. A compound of formula I

(I)

[Chemical structure of formula I showing a macrocyclic milbemycin skeleton with substituents labeled: RCS(=O) at position 13, CH3 groups, OR1, OH, H, R2, and positions 5, 8, 13, 17 marked]

in which $R_1$ is a hydrogen or a silyl or acyl group, $R_2$ is methyl, ethyl, isopropyl or sec.-butyl and R is hydrogen, unsubstituted or substituted, linear or branched-chain $C_1$–$C_{18}$-alkyl groups, unsubstituted or substituted cycloaliphatic groups having 3 to 10 carbon atoms, unsubstituted or substituted $C_2$–$C_6$-alkenyl groups, unsubstituted or substituted $C_2$–$C_6$-alkynyl groups, unsubstituted or substituted phenyl groups or unsubstituted or substituted benzyl groups, the substituents of said alkyl, cycloaliphatic, alkenyl and alkynyl R-groups being 1 to 7 halogen atoms or 1 to 6 $C_1$–$C_6$-alkoxy groups and the substituents of the phenyl and benzyl R-groups being 1 to 3 substituents selected from the group consisting of halogen atoms, $C_1$–$C_6$-alkyl, $C_1$–$C_6$-alkoxy, $C_1$–$C_4$-alkylthio, phenyl and nitro.

2. A compound of the formula I, according to claim 1, in which $R_1$ is hydrogen, $R_2$ is methyl, ethyl, isopropyl or sec.-butyl and R is hydrogen or $C_1$–$C_6$-alkyl, $C_2$–$C_4$-alkenyl, $C_2$–$C_4$-alkynyl or $C_3$–$C_6$-cycloalkyl, each of which is unsubstituted or substituted by 1 to 4 halogen atoms or by $C_1$–$C_4$-alkoxy; or R is phenyl which is unsubstituted or monosubstituted to trisubstituted by halogen, $C_1$–$C_4$-alkyl, $C_1$–$C_4$-alkoxy, $C_1$–$C_4$-alkylthio or nitro.

3. A compound of the formula I, according to claim 1, in which $R_1$ is hydrogen, $R_2$ is methyl or ethyl and R is $C_1$–$C_7$-alkyl, $C_1$–$C_4$-alkyl which is monosubstituted by chlorine, fluorine, methoxy, methylthio, dimethylcyclohexyl or acetyl, phenyl which is monosubstituted by trifluoromethyl or the group —O—$CF_2$—O— in which the two oxygen atoms are located on two adjacent ring carbon atoms, phenyl which is monosubstituted to trisubstituted by substituents of the group consisting of chlorine and methyl, or α-methylbenzyl or α,α-dimethylbenzyl, each of which is unsubstituted or substituted by 1 to 3 substituents of the group consisting of amino, halogen, $C_1$–$C_6$-alkyl, $C_1$–$C_6$-alkoxy, $C_1$–$C_4$-alkylthio, phenyl and nitro.

4. A compound of the formula I, according to claim 1, in which $R_1$ is hydrogen, $R_2$ is methyl or ethyl and R is $C_1$–$C_7$-alkyl which is unsubstituted or monosubstituted by halogen or $C_1$–$C_4$-alkoxy, phenyl which is monosubstituted by trifluoromethyl or the group —O—$CF_2$—O— in which the two oxygen atoms are located on two adjacent ring carbon atoms, or is α-methylbenzyl or α,α-dimethylbenzyl.

5. A compound of the formula I, according to claim 1, in which $R_1$ is hydrogen, $R_2$ is methyl or ethyl and R is $C_1$–$C_7$-alkyl, $C_1$–$C_4$-alkyl which is monosubstituted by chlorine, fluorine or methoxy, phenyl which is monosubstituted by trifluoromethyl or the group —O—$CF_2$—O— in which the two oxygen atoms are located on two adjacent ring carbon atoms, or is α-methylbenzyl or α,α-dimethylbenzyl.

6. A compound of the formula I, according to claim 1, in which $R_1$ is the radical —Si($R_6$)($R_7$)($R_8$), in which $R_6$, $R_7$ and $R_8$ independently of one another are $C_1$–$C_4$-alkyl, benzyl or phenyl, and R and $R_2$ are as defined in claim 1.

7. A compound of the formula I, according to claim 1, in which $R_1$ is a radical from the group consisting of trimethylsilyl, diphenyl-tert.-butylsilyl, bis-(isopropyl)-methylsilyl, triphenylsilyl and tert.-butyldimethylsilyl.

8. A compound of the formula I, according to claim 1, in which $R_1$ is the radical $R_5$—C(O)—, in which $R_5$ is $C_1$–$C_{10}$-alkyl, $C_1$–$C_{10}$-halogenoalkyl or a radical from the group consisting of phenyl and benzyl which is unsubstituted or substituted by substituents of the group consisting of halogen, $C_1$–$C_3$-alkyl, $C_1$–$C_3$-halogenoalkyl, $C_1$–$C_3$-alkoxy, $C_1$–$C_3$-halogenoalkoxy, cyano and nitro, and R and $R_2$ are as defined in claim 1.

9. A compound according to claim 1, selected from the group consisting of:
13β-Formylthiomilbemycin D
13β-Acetylthiomilbemycin D
13β-Pivaloylthiomilbemycin D
13β-Formylthiomilbemycin $A_3$
13β-Acetylthiomilbemycin $A_3$
13β-Pivaloylthiomilbemycin $A_3$
13β-Formylthiomilbemycin $A_4$
13β-Acetylthiomilbemycin $A_4$
13β-Pivaloylthiomilbemycin $A_4$
13β-(2'-Methoxy-2'-methylpropionylthio)-milbemycin D
13β-(2'-Methoxy-2'-methylpropionylthio)-milbemycin $A_4$
13β-Trichloroacetylthiomilbemycin $A_4$
13β-(4'-Chlorobutanoylthio)-milbemycin $A_4$
13β-Trichloroacryloylthiomilbemycin $A_4$
13β-Cyclopropanecarbonylthiomilbemycin $A_4$
13β-Cyclobutanecarbonylthiomilbemycin $A_4$
13β-Heptanoylthiomilbemycin $A_4$
13β-(3'-Chloro-2',2'-dimethylpropionylthio)-milbemycin $A_4$
13β-(3'-Chloro-2',2'-dimethylpropionylthio)-milbemycin $A_3$
13β-(1'-Methylcyclopropanecarbonylthio)-milbemycin $A_4$
13β-(1'-Methylcyclopropanecarbonylthio)-milbemycin $A_3$
13β-(1-Adamantanecarbonylthio)-milbemycin $A_4$
13β-(p-Fluorophenoxyacetylthio)-milbemycin $A_4$
13β-(2'-Chloro-2'-methylpropionylthio)-milbemycin $A_4$
13β-(2',2'-Dichloropropionylthio)-milbemycin $A_4$
13β-(2',2'-Dimethylbutanoylthio)-milbemycin $A_4$
13β-(3',3'-Dimethylbutanoylthio)-milbemycin $A_4$
13β-(2',2',3',3'-Tetramethylbutanoylthio)-milbemycin $A_4$
13β-(p-Chlorobenzoylthio)-milbemycin $A_4$
13β-(3',3',3'-Trifluoropropionylthio)-milbemycin $A_4$ 13β-Chloroacetylthiomilbemycin A₄
13β-(2'-Chloro-3',3',3'-trifluoropropionylthio)-milbemycin A₄
13β-(3',3',3'-Trifluoropropionylthio)-milbemycin A₄
13β-[o-(Trifluoromethyl)-benzoylthio]-milbemycin A₄
13β-(α,α-Dimethylbenzoylthio)-milbemycin A₄
13β-(2-n-Propyl-n-valeroylthio)-milbemycin A₄
13β-[(2,3-Difluoromethylenedioxy)-benzoylthio]-milbemycin A₄
13β-(α-Methylbenzylcarbonylthio)-milbemycin A₄ and
13β-(Methoxyacetylthio)-milbemycin A₄.

10. A compound according to claim 1, selected from the group consisting of:
5-O-tert.-Butyldimethylsilyl-13β-formylthiomilbemycin D
5-O-tert.-Butyldimethylsilyl-13β-acetylthiomilbemycin D
5-O-tert.-Butyldimethylsilyl-13β-pivaloylthiomilbemycin D
5-O-tert.-Butyldimethylsilyl-13β-formylthiomilbemycin A₃
5-O-tert.-Butyldimethylsilyl-13β-acetylthiomilbemycin A₃
5-O-tert.-Butyldimethylsilyl-13β-pivaloylthiomilbemycin A₃
5-O-tert.-Butyldimethylsilyl-13β-formylthiomilbemycin A₄
5-O-tert.-Butyldimethylsilyl-13β-acetylthiomilbemycin A₄
5-O-tert.-Butyldimethylsilyl-13β-pivaloylthiomilbemycin A₄
5-O-tert.-Butyldimethylsilyl-13β-(2'-methoxy-2'-methylpropionylthio)-milbemycin D
5-O-tert.-Butyldimethylsilyl-13β-(2'-methoxy-2'-methylpropionylthio)-milbemycin A₄
5-O-tert.-Butyldimethylsilyl-13β-trichloroacetylthiomilbemycin A₄
5-O-tert.-Butyldimethylsilyl-13β-(4'-chlorobutanoylthio)milbemycin A₄
5-O-tert.-Butyldimethylsilyl-13β-trichloroacryloylthiomilbemycin A₄
5-O-tert.-Butyldimethylsilyl-13β-cyclopropanecarbonylthiomilbemycin A₄
5-O-tert.-Butyldimethylsilyl-13β-cyclobutanecarbonylthiomilbemycin A₄
5-O-tert.-Butyldimethylsilyl-13β-heptanoylthiomilbemycin A₄
5-O-tert.-Butyldimethylsilyl-13β-(3'-chloro-2',2'-dimethylpropionylthio)-milbemycin A₄
5-O-tert.-Butyldimethylsilyl-13β-(3'-chloro-2',2'-dimethylpropionylthio)-mibemycin A₃
5-O-tert.-Butyldimethylsilyl-13β-(1'-methylcyclopropanecarbonylthio)-milbemycin A₄
5-O-tert.-Butyldimethylsilyl-13β-(1'-methylcyclopropanecarbonylthio)-milbemycin A₃
5-O-tert.-Butyldimethylsilyl-13β-(1-adamantanecarbonylthio)milbemycin A₄
5-O-tert.-Butyldimethylsilyl-13β-(p-fluorophenoxyacetylthio)milbemycin A₄
5-O-tert.-Butyldimethylsilyl-13β-(2'-chloro-2'-methylpropionylthio)-milbemycin A₄
5-O-tert.-Butyldimethylsilyl-13β-(2',2'-dichloropropionylthio)-milbemycin A₄
5-O-tert.-Butyldimethylsilyl-13β-(2',2'-dimethylbutanoylthio)-milbemycin A₄
5-O-tert.-Butyldimethylsilyl-13β-(3',3'-dimethylbutanoylthio)-milbemycin A₄
5-O-tert.-Butyldimethylsilyl-13β-(2',2',3',3'-tetramethylbutanoylthio)-milbemycin A₄
5-O-tert.-Butyldimethylsilyl-13β-(p-chlorobenzoylthio)-milbemycin A₄
5-O-tert.-Butyldimethylsilyl-13β-(3',3',3'-trifluoropropionylthio)-milbemycin A₄
5-O-tert.-Butyldimethylsilyl-13β-chloroacetylthiomilbemycin A₄
5-O-tert.-Butyldimethylsilyl-13β-(2'-chloro-3',3',3'-trifluoropropionylthio)-milbemycin A₄
5-O-tert.-Butyldimethylsilyl-13β-(3',3',3'-trifluoropropionylthio)-milbemycin A₄
5-O-tert.-Butyldimethylsilyl-13β-(α-methylbenzylcarbonylthio)-milbemycin A₄
5-O-tert.-Butyldimethylsilyl-13β-(methoxyacetylthio)-milbemycin A₄
5-O-tert.-Butyldimethylsilyl-13β-[o-(trifluoromethyl)-benzolythio]-mibemycin A₄
5-O-tert.-Butyldimethylsilyl-13β-(α,α-dimethylbenzoylthio)milbemycin A₄
5-O-tert.-Butyldimethylsilyl-13β-(2-n-propyl-n-valeroylthio)milbemycin A₄
5-O-tert.-Butyldimethylsilyl-13β-[(2,3-difluoromethylenedioxy)-benzoylthio]-milbemycin A₄.

11. An agent for the control of pests on animals and plants, which, in addition to carriers, distribution agents or agents for carrying and distribution, contains at least one compound of the formula I according to claim 1 as the active substance.

12. A process for the control of pests on animals and plants, wherein a pesticidally effective amount of at least one compound of claim 1 is applied to habitats of the pests.

13. A process according to claim 12, wherein the pests to be combated are endoparasites or ectoparasites which infest animals.

14. A process according to claim 12, wherein the pests to be combated are parasites which damage plants.

15. A process according to claim 12, wherein the habitats of the pests are host animals and host plants.

* * * * *